United States Patent [19]

McLaughlin

[11] 4,196,614
[45] Apr. 8, 1980

[54] PROCESS AND DEVICE FOR QUANTITATIVE ANALYSIS OF CEMENT AND WATER CONTENT IN FRESH CONCRETE

[76] Inventor: Robert R. McLaughlin, Baranangsiang, Bogor, Indonesia

[21] Appl. No.: 870,880

[22] Filed: Jan. 20, 1978

[51] Int. Cl.² ............................................. G01N 15/00
[52] U.S. Cl. ........................................ 73/61 R; 73/73
[58] Field of Search .................................. 73/73, 61 K

[56] References Cited

U.S. PATENT DOCUMENTS

| | | | |
|---|---|---|---|
| 2,357,083 | 8/1944 | Clagett | 73/54 |
| 2,372,595 | 3/1945 | Maxon | 73/54 |

*Primary Examiner*—Anthony V. Ciarlante
*Attorney, Agent, or Firm*—John T. Roberts

[57] ABSTRACT

A process and associated meter devices which will provide accurate and rapid measurement of the quantities of cement and water in a sample of fresh concrete. A special volumetric flask is filled with a sample of fresh concrete to a known volume. The volumetric flask and its contents are then attached to the hollow body of a shaker meter which forms an extension of the upper part of the volumetric flask. A predetermined volume of special mixing liquid with precisely known density different than water is then added and thoroughly mixed with the concrete sample by shaking. A portion of the resulting cement-water-mixing liquid suspension, or liquor, is then poured off and strained into a vial where its relative density, which is a function of the amount of each constituent present, is determined by a special hydrometer. Another portion of the resulting suspension, or liquor, is filtered through a suitable paper, or other material, so that all cement is removed. The relative density of the filtrate is a function only of the amounts of free water and mixing liquid present in the original concrete sample and their densities. The same special hydrometer is used to measure the density of the filtrate and particular equations which have been developed for use in this invention can then be applied to accurately determine the amounts of cement and water contained in the original concrete sample.

1 Claim, 5 Drawing Figures

PROCESS AND DEVICE FOR QUANTITATIVE ANALYSIS OF CEMENT AND WATER CONTENT IN FRESH CONCRETE

CROSS-REFERENCE TO RELATED APPLICATION

This invention is not disclosed in any co-pending application for a patent or any issued patent.

FIELD OF THE INVENTION

The strength of concrete is affected by many factors which may vary widely. The three principle constituents cement, water and aggregate, may be present in various ratios and may be of various types or quality. Other factors such as mixing, handling and curing conditions will also have considerable influence on the strength of the concrete at any age after casting. One of the most important factors in the composition of concrete is the relative proportion of water to cement in the mixture at the time of casting. This relationship is referred to by the special term "water/cement ratio", which is usually expressed in engineering literature simply by the symbol "W/C". It is the ratio of the weight of free water in the mixture which has combined with the cement to produce the paste which binds the mass.

A small increase in the water/cement ratio can profoundly decrease the potential strength and quality of concrete. For instance, concrete placed with a water/cement ratio of 0.35 could be expected to achieve a compressive strength of 450 kg/sq cm whereas the same mixture placed with a water/cement ratio of 0.50 might only achieve a compressive strength of 350 kg/sq cm at the same age. But the first mentioned mixture would be too dry for placement under ordinary casting procedures in the field and so more water must be added. In order to achieve proper workability of the concrete mixture without unduly increasing the cement content the water/cement ratio must be increased. Engineers have had to accept this fact and concrete mixes are designed on the basis of the water/cement ratio required to achieve the design strength and then proportioning the ingredients so that the final mix is workable and does, in fact, contain water and cement in that exact ratio.

It might seem that once the water/cement ratio for a particular mixture is specified there is no further problem, but that is not the case. In careful practice all of the ingredients of a concrete batch are accurately weighed as they are loaded into the mixer. But spurious water may enter the mixture as a film on the aggregates, as a result of faulty equipment or in a later attempt to make the mixture more workable. Conversely, water may be lost from the mixture by evaporation, drier aggregates or faulty equipment. In the first case detection of the increased water/cement ratio would allow correction of a potentially dangerous or costly situation, for if subsequent strength tests were substandard, concrete would have to be removed or perhaps accepted at a reduced price. In the second case the mixture would become too dry for easy or proper placement. Since concrete is often placed at some distance from where it is mixed dilemmas often develop as to whether or not it is permissible to add water at the jobsite in order to make the mixture workable or whether the allowable water/concrete ratio would thereby be exceeded. A conservative solution to these dilemmas often causes difficult, improper placement or wasting of the fresh concrete rather than incurring the risk of exceeding the specified water/cement ratio. A simple and quick means to actually measure the water/cement ratio of the concrete mixture in the field would eliminate such dilemmas.

Previous Developments

Until now, the water/cement ratio of a fresh concrete mixture has not been measured by a field test. The supposed water/cement ratio has been assumed based on faith in the batching equipment and measurements of the moisture content of the aggregates. Although these measurements may be very good when and where they are made, they may not be applicable later in a hot day or after the concrete has been transported over some distance. In order to check the apparent water content of the concrete mixture tests of its consistency are used.

The most widely used test for consistency is the Slump Test. A sample of fresh concrete is tamped into a truncated cone, with open top and bottom, resting on a level base. When the cone is full it is lifted so that the contents are left standing on the base slab without side support. The amount to which the concrete slumps down is a measure of its consistency and is considered an indication of the water content of the mixture.

Another test for consistency, which is often used, is the Ball Penetration Test. A sample of fresh concrete in place or in a container is given a level surface. A standard-sized steel plunger with a ball-shaped tip is positioned above the concrete and a graduated sliding rod is set at a reference mark when the lower face of the plunger makes contact with the upper surface of the fresh concrete. The plunger is then released and the amount of penetration of the ball into the concrete mixture by its own weight is a measure of the consistency of the concrete mixture and is considered an indication of its water content.

These tests have been and will continue to be valuable for control of concrete mixtures in the field because they answer the question of whether or not the concrete is workable or the water content seems to be excessive. But, if the question is really whether or not the water/cement ratio is correct, then those tests do not give the answer. What has been missing is a fast and simple process for direct analysis of the water/cement ratio in the field. The process and equipment of my invention provide the means to make that analysis.

It has always been possible, of course, to separate the solid constituents of concrete from each other by using sieves and washing. The constituents could then be dried and weighed and calculations involving the original weight of the concrete sample versus the dry weights of the solid constituents could be made to yield the original composition including the water and cement. But such a test is not suited for field conditions because of the equipment and amount of time required to sieve and dry the samples. The use of this method has been confined to the laboratory.

BRIEF DESCRIPTION OF THE INVENTION

In my invention separation of the constituents is accomplished by suspension of the cement sized particles and mixture of the original water content of the concrete by shaking together with a special mixing liquid. Larger particles of aggregate and sand settle quickly to the bottom of this suspension and a strainer of appropriate fineness is used to further remove unwanted particles. The cement-water-mixing liquid suspension thus obtained is poured into a vial and its relative density determined by special hydrometer. I call this suspension the Liquor, and denote its relative density by the symbol $M_{LIQ}$. The liquor is then filtered to remove all nonliquid constituents and the relative density of the liquid phase is also determined by special hydrometer. I call this phase the Filtrate and denote its relative density by the symbol $M_{FILT}$. At this point, using the data obtained, the equations which I have developed in my invention, and the values of 3 basic properties of the cement, the total amounts of water and cement in the original concrete sample can be calculated. Because the volume of the sample is known to be that of the volumetric flask, the results can be extrapolated to any other volume, such as one cubic meter of concrete.

The usual system of measure for relative density is specific gravity. In this system every substance is said to have a specific gravity equal to the ratio of its absolute density compared to that of water. Therefore, water has a specific gravity=1.000. Furthermore, since water has a standard density of 1.000 grams per cubic centimeter, its weight in grams always equals its volume in cubic centimeters under standard conditions. For the purpose of this discussion it is assumed that these standard conditions pertain and that all measurements are made in the metric system of units. However, for reasons which will be more fully explained hereinafter, relative density will be expressed in terms relative to specific gravity by the following definite relationship:

$$M = (SG-1)/(SG)$$

in which equation M denotes the Buoyancy Point of a substance and SG denotes the Specific Gravity of the substance.

The three basic properties of the cement which must be known are easily obtained by simple experiments. It is anticipated that cement suppliers will furnish the values for their products when this method comes into general use. The three properties are as follows: (1) Buoyancy Point of the cement, which I denote by the symbol $M_{CEM}$; (2) Solubility Factor of the cement, which I denote by the symbol $S_{CEM}$; and (3) Absorption Factor of the cement, which I denote by the symbol $A_{CEM}$. The first of these properties, $M_{CEM}$, is fairly constant for all cements and usually has a value near 0.683. The second of these properties, $S_{CEM}$, depends on the solubility of cement components. These components are generally only slightly soluble hydroxides, sulfates, and carbonates which reach equilibrium concentration with the ubiquitous calcium ion from the cement long before they fully dissolve. Therefore, the value of $S_{CEM}$ does not vary greatly among cements of different source unless some special constituent is present. The method of measurement for $S_{CEM}$ is to determine the Buoyancy Point, $M_{SOL}$, of a saturated solution filtered from a cement and water mixture. Then, $$S_{CEM} = 1/1(-M_{SOL})$$

and my experimental results have yielded values close to 1.005. The third cement property, $A_{CEM}$, can vary considerably among cements of different composition, type and fineness. When cement is first mixed with water it absorbs some of the water so that only a portion of the original water present in the concrete remains free to suspend the particles or to mix with other ingredients. This absorption occurs almost immediately when the cement and water come together and does not change appreciably in the first two or more hours after mixing and before setting occurs. The amount of absorption for any particular cement is a function of its weight. The value of $A_{CEM}$ is the weight of water absorbed divided by the weight of cement. My experiments have yielded values for $A_{CEM}$ from near zero to several percent.

Of course, there are other factors which could interfere with proper readings. Additives of pozzolan, fly ash, or calcium chloride in the mixture could cause false readings but they are easily allowed for in the formulae. The formulae are simply based on the relationships between relative densities of substances and their mixtures.

BRIEF DESCRIPTION OF DRAWINGS

The process and operation of my invention will become more fully apparent as the description is read in conjunction with the accompanying drawings.

DETAILED DESCRIPTION OF THE INVENTION

Figure 2:
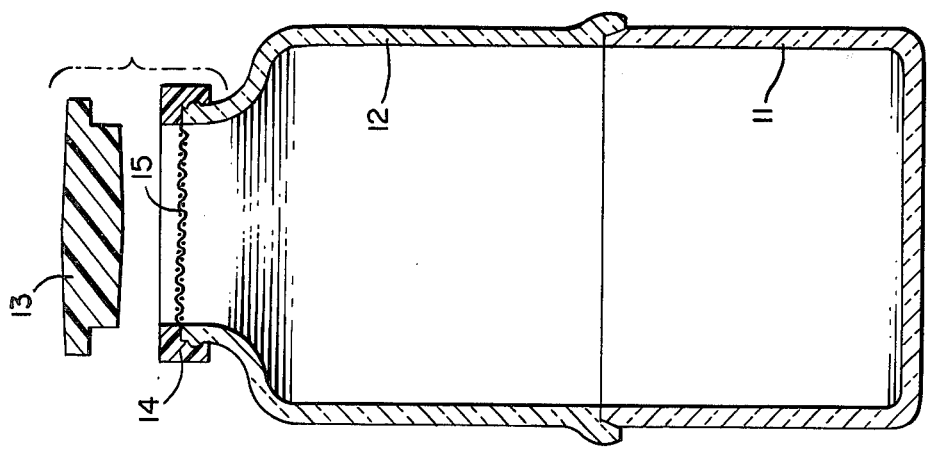
FIG. 2 is a cross-sectional view of the same shaker meter showing details of its construction including the detachable volumetric base and strainer cap in place.
Figure 1:
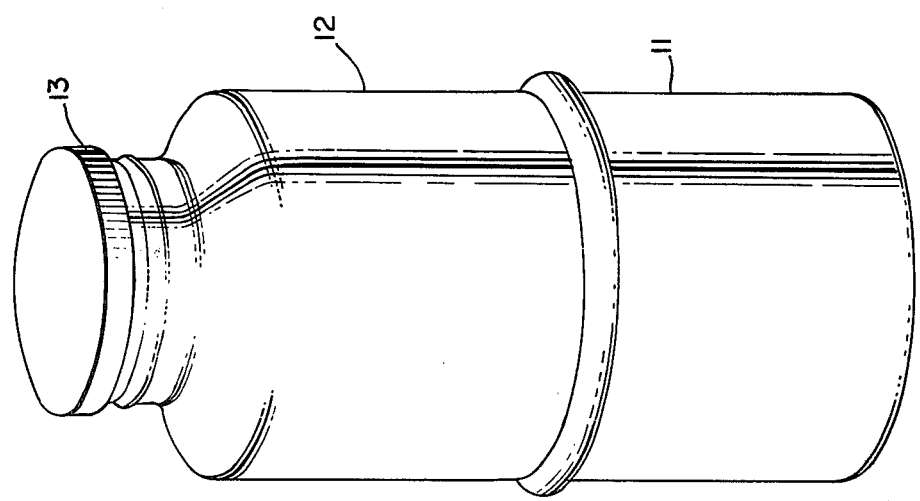
FIG. 1 is a perspective view of a shaker meter with shaker cap in place in one of the many possible configurations for use in the present invention.

Referring now in detail to the several figures, the preferred embodiment of a shaker meter for use in my invention is shown in FIG. 1 as it would appear ready for use. FIG. 2 is a cross-sectional view of the same meter showing details of construction.

The particular configuration in FIG. 2 comprises a volumetric base, 11, shaker body, 12, shaker cap, 13, strainer cap, 14, and strainer, 15.

All of the elements are preferably of circular shape and adjoining elements mate closely with one another to provide a postive seal against leakage. Volumetric base, 11, shaker body, 12, shaker cap, 13, and strainer cap, 14, are preferably made of tough, rigid, transparent or semitransparent plastic or polycrystalline glass. Toughness is desirable because those parts will be subjected to impact and abrasion by the concrete aggregate when it is shaken inside. Rigidity is required to maintain volumetric relationships and fit of mating parts. Transparency is desirable to be able to observe the contents of volumetric base, 11, to make sure there are no voids in the concrete sample. Transparency will also allow observation of the degree of mixing of the concrete sample and the special mixing liquid when they are shaken together. It is essential that the mixing be complete before the liquor sample is poured off.

Strainer, 15, can be made of metal, plastic or fabric. Strainer, 15, can either be relatively coarse or relatively fine, depending on whether or not an external strainer is also used. In case strainer, 15, is to be the only strainer in the system, it should be of about 1 millimeter mesh opening size. Where a second, finer strainer is used in tandem with strainer, 15, the openings should be 2 to 3 millimeters in size. In either case the purpose of the strainer system is to limit the size of particle included in the liquor poured off after shaking concrete sample and special mixing liquid together. Strainer, 15, must not be too fine or else it will quickly clog and the liquor sample will not be representative.

Care must be exercised to obtain a truly representative sample of the liquor, which comprises a suspension of cement particles in the special mixing liquid diluted by the original water of the concrete sample. Uniformity of the sample is enhanced by careful pouring through strainer, 15, and frequent agitation to prevent blockage. An excess of liquor should be poured off into a flask so that it can be agitated just prior to placing in the hydrometer vial for relative density measurement. The tendency for the suspended cement particles to settle toward the bottom is inversely proportional to their size and the viscosity of the medium, according to the well-known Stokes Law. Because the cement particles are very small and the special mixing liquid has a much higher viscosity than water, the settlement rate in this process is very slow and accurate results can be obtained.

Figure 4:
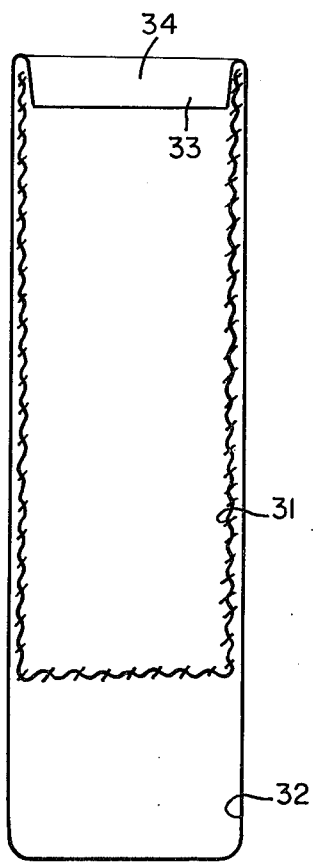
FIG. 4 is a cutaway view of a strainer sock assembly with plastic retainer for exclusion of fine aggregate particles from the liquor sample.

Under most circumstances the accuracy of density measurements of the liquor can be enhanced by further limiting the amount of fine aggregate particles which might enter the liquor sample. This can be achieved by use of a secondary strainer system. The secondary strainer system must not, however, inhibit the free flow of a uniform liquor sample. FIG. 4 shows the preferred embodiment of such a secondary system in the form of a strainer sock enclosed in a plastic retainer.

The elements comprising the device of FIG. 4 are strainer sock, 31, retainer, 32, closure, 33, and top opening, 34. Strainer sock, 31, is made of relatively flexible synthetic fabric such as polyester, acetate, nylon, etc. The fabric is woven to provide a particular mesh opening in the preferred range of 0.05 to 0.50 millimeters. Retainer, 32, is a transparent plastic bag of polyethylene or other suitable material, preferably 0.05 to 0.1 millimeters thick. Both strainer sock, 31, and retainer, 32, are of tubular form when expanded for use and of flat form when in storage. They have closed bottom portions and a common top opening, 34. Closure, 33, is the connection between strainer sock, 31, and retainer, 32, which is made by thermal fusion or by adhesive.

The advantage of this particular embodiment of a secondary strainer system will now be explained. When the primary liquor sample is collected it may still contain considerable aggregate particles because of the size of the openings in strainer, 15. Simply pouring the sample into a strainer with smaller openings is not satisfactory because the openings quickly become clogged or restricted to the point that the sample passes very slowly and the cement Particles are partially retained. In the embodiment of FIG. 4, the primary liquor sample is poured into top opening, 34, and the desired suspension begins to pass through strainer sock, 31, after which it is collected in retainer, 32. As the secondary liquor sample is collecting between retainer, 32, and strainer sock, 31, the entire assembly is kneaded by the fingers so as to wash the sample in and out of strainer sock, 31. Careful kneading for the period of secondary liquor collection will assure that the cement-water-mixing liquid suspension is uniform on both sides of the strainer. When sufficient uniform liquor sample has accumulated in retainer, 32, the bottom is cut or punctured to allow the liquor sample to be transferred. It is intended that the strainer sock assembly be discarded after a single use.

Figure 5:
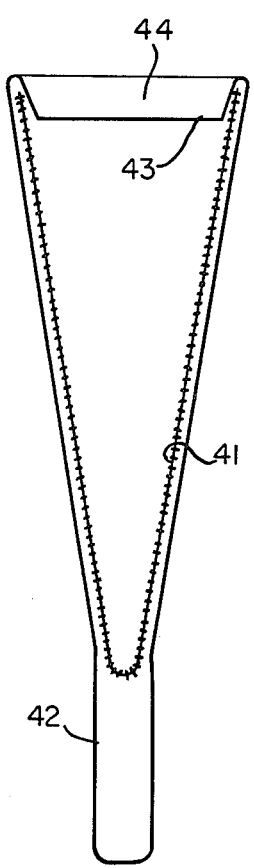
FIG. 5 is a cutaway view of a filter assembly for production of filtrate from the liquor.

FIG. 5 shows a filter assembly for separating the suspended solid particles from the liquid component of the liquor and thus producing the filtrate. The filter assembly comprises filter cone, 41, sleeve, 42, closure, 43, and top opening, 44. Filter cone, 41, is of filter paper or filter cloth of types readily available and normally used in chemical processes. The pores must be fine enough to retain particles of 0.01 millimeter diameter but the passage of liquid component should be as rapid as possible. Sleeve, 42, is of transparent plastic material, similar to that of retainer, 32. The upper portion of sleeve, 42, is shaped conically to support filter cone, 41, which may be quite weak when wet. The bottom portion of sleeve, 42, forms a reservoir of the filtrate or, alternatively, it may be open at the bottom so that filtrate can pass directly into a vial. Closure, 43, is the connection between filter cone, 41, and sleeve, 42, which is made by thermal fusion or by adhesive.

A portion of liquor is poured into top opening, 44, and the liquid phase begins to pass through filter cone, 41. Filtrate collects in the bottom of sleeve, 42, or passes through into a vial when opened. It is intended that the filter assembly be discarded after a single use.

The special mixing liquid which I prefer comprises a solution of sugar in water which has previously been saturated by the soluble constituents of cement. The special mixing liquid preferred has a Buoyancy Point $M = 0.1667$, and the volume preferred is 250 cc per liter of concrete sample. The results thus obtained are well defined and graphs used for solving equations (1) and (2) have good resolution. For instance, an accuracy in the hydrometer readings of $\pm 0.001$ M, which is not unusual, will yield accuracies in $W_{CEM}$ and WOW of about $\pm 2\%$.

There are many other solutions which would serve equally well. They might have a specific gravity either higher or lower than water but they must be miscible with water and non-reactive with the cement during the period of the test.

Principles other than specific gravity can be applied to determine the percentage dilution of the mixing liquid by the original water of the concrete. One method would be to use a mixing liquid containing a precise concentration of radioactive material which would be detectable by a standard counter according to the emission rate. Dilution of the mixing liquid by the original water of the concrete sample would cause a proportionate decrease in the emission rate detected in the filtrate. Another method would be to use a mixing liquid containing a particular concentration of a specific ion not likely to be present in the concrete in significant amounts. An example might be uranium ion. The ion concentration in the mixing liquid before and after dilution by the original water of the concrete sample could be measured in the filtrate by specific ion meters of electronic type currently on the market. This would also be proportionate to the percentage dilution and so would serve as an accurate measure of the original water content of the concrete.

For ordinary concrete and the preferred proportion of special mixing liquid the resulting values of $M_{LIQ}$ and $M_{FILT}$ may be anywhere from 0.400 down to 0.050.

Unless a number of fairly large hydrometers are available, sensitive measurements cannot be made covering such a wide range. Also, if such large hydrometers are used, the amount of sample required will also be large in order to fully immerse a long graduated stem. This is especially inconvenient with regard to measurement of $M_{FILT}$ because the total time required to perform the entire analysis depends in large part on the time required to filter that sample. The clogging effect of cement particles in the filter paper and the rather viscous mixing liquid slow the filtration. In order to cover the entire range of anticipated relative densities with a single hydrometer, and in order to limit the amount of sample required for an accurate measurement, this invention includes an adjustable range hydrometer device.

Figure 3:
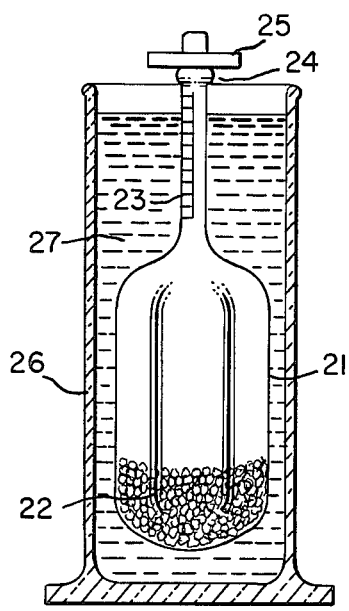
FIG. 3 is a cut-away elevation view of an adjustable range hydrometer based on the "Buoyancy Points" system of graduation for accurate measurements related to relative density over an extended scale range.

FIG. 3 shows an adjustable range hydrometer as it would be used to measure the relative densities of the liquor and filtrate samples in this invention. The particular configuration of FIG. 3 comprises a body, 21, ballast, 22, graduated stem, 23, weight boss, 24, add-on weight, 25, and sample vial, 26. The hydrometer body, 21, stem, 23, and weight boss, 24, are of one-piece glass construction with hollow, circular configuration in cross-section. Ballast, 22, is of heavy metal beads stabilized by wax, thermoplastic or adhesive. The relative sizes, shapes, weights and positions of the various elements are selected so that the hydrometer will be properly buoyant and stable under the required service conditions. Add-on weight, 25, is one of a series of brass washers which are added individually to change the rate of the graduations of stem, 23. Weight boss, 24, is a protuberance of stem, 23, which provides a shoulder support for add-on weight, 25. The greater the mass of add-on weight, 25, the higher the range of relative density values represented by the graduations of stem, 23. The useful range of the adjustable hydrometer is determined by its stability. If the amount of weight added to the top of stem, 23, creates an unstable condition of buoyancy, the hydrometer will not float upright and will yield unreliable readings. Stability of the hydrometer is enhanced by lowering either ballast, 22, or weight, 25, with respect to the liquid surface and by raising the center of buoyancy of body, 21.

An adjustable hydrometer of the type described herein cannot be graduated directly in values of specific gravity. The nature of the specific gravity function is such that the graduations of stem, 23, would have to be spaced differently as the scale range was either increased or decreased. This can be accomplished by using removable insert graduations inside stem, 23, which would have to be changed each time a different add-on weight, 25, is used to change the scale range of the hydrometer. In order to avoid this inconvenience, a different approach has been followed in the embodiment shown in FIG. 3. In this case, a scale is used in which the graduations of stem, 23, are linearly related or equally spaced, over the entire range from the least density to the greatest density. Although the well-known Baume scale is such a linear scale, it is not continuous over a wide range and its relationship to specific gravity is not as simple as might be desired. Therefore, in my invention I use graduations based on the scale of Buoyancy Points as hereinbefore described. It has already been stated that the Buoyancy Point, M, of an object relates to its specific gravity, SG, according to the equation:

$$M = (SG-1)/SG$$

which can also be stated:

$$M = 1 - (VOLUME/WEIGHT)$$

It can be seem from this relationship that the value of M corresponding to the SG of pure water is zero. The values of M for fluids, solids or gases less dense than water are always negative, and, for those more dense, M is always positive. A hydrometer graduated by Buoyancy Points will always sink in a fluid until the graduation at the liquid level, denoted by $M_{GRAD}$, represents $$M_F = 1 - (V_o/W_T) + M_{GRAD}$$

In which equation $M_F$ denotes the Buoyancy point of the immersion fluid, $V_o$ denotes the total volume of the hydrometer below the zero graduation, and $W_T$ denotes the total weight of the hydrometer including add-on weights. It can be readily seen that $V_o$ is constant for a particular hydrometer. $W_T$ can be varied in stages so that $M_F$ corresponding to an $M_{GRAD}$ reading of zero can be made to correspond to values of $M_F$ in any desired increments and ranges. Using this system the flexibility of scale ranges and the accuracy of measurements are enormously increased, while the amount of fluid sample required is considerably decreased.

Accuracy, or sensitivity, of hydrometer measurements, is a function of the total immersed volume of the hydrometer versus the cross-sectional area of the graduated stem, 23. The greater that ratio, the more widely spaced will be the scale graduations, and therefore, the more sensitive the readings. However, in an ordinary hydrometer, if the ratio is very great, graduated stem 23 will necessarily be very long which will make the hydrometer unwieldy, fragile and require large sample volumes for immersion. The adjustable hydrometer in the present invention allows the use of a high body volume to stem area ratio and a short stem length because the scale is broken into increments by the use of add-on weights.

In addition to those advantages, it is only necessary to carry a single adjustable range hydrometer to perform all density measurements required in the process of the present invention.

DETAILED DESCRIPTION OF THE PROCESS

Equipment and materials required in the process of this invention include one complete shaker meter, as shown in FIGS. 1 and 2; one adjustable range hydrometer device, as shown in FIG. 3, complete with vial and add-on weights to cover the range of Buoyancy Points from M=0.00 to M=0.40; a volume of special mixing liquid; one complete strainer sock assembly as shown in FIG. 4; one complete filter cone assembly as shown in FIG. 5; and such miscellaneous flasks, funnels, bucket, wiping rags, cleanup water, etc. as desired.

The process is begun by scooping a sample of recently mixed concrete into the bucket. After it has been re-mixed to assure uniformity, the volumetric base, 11, of the shaker meter is filled with the concrete sample to an exact volume without voids. The volumetric base is then attached to the shaker body, 12, and the predetermined volume of special mixing liquid is added through the open top of the shaker body, 12. Shaker cap, 13, is then inserted and the concrete sample and special mixing liquid are vigorously agitated together inside the closed meter by shaking. After an appropriate length of time, usually about one minute, when the mixture is seen to be complete, shaker cap, 13, is removed and strainer cap, 14, and strainer, 15, are placed over the opening of the top of shaker body, 12. A portion of the liquor sample inside the shaker meter is then carefully poured through strainer, 15, into top opening, 34, of the strainer sock assembly. The remainder of the liquor is poured into the top opening, 44, of the filter assembly to begin collection of filtrate sample. As the secondary liquor sample begins to collect inside retainer, 32, the strainer sock, 31, and its contents, are gently but firmly kneaded with the fingers to bring into balance the composition of the liquor suspension on both sides of strainer sock, 31. When sufficient sample of proper quality has been collected in retainer, 32, it is punctured and the liquor sample transferred to vial, 26. The Buoyancy Point of the liquor sample is measured by inserting the adjustable range hydrometer into the liquor sample in vial, 26, selecting the add-on weight, 25, which yields a reading on graduated stem, 23, and recording the result. $M_{LIQ}$ is the sum of the add-on weight range value plus the graduation reading. The liquor sample is then discarded and the hydrometer and vial are rinsed and wiped clean. The collected filtrate sample is then emptied into hydrometer vial, 26, and its relative density is measured in the same manner. The result is recorded as $M_{FILT}$.

The absolute weights of water and cement present in the original concrete sample of volumetric base, 11, can now be readily obtained either by directly solving equations or by referring to a graph relating the observed and sought values. A graph with values of $M_{LIQ}$ as abcissa and $M_{FILT}$ as ordinates, can be made to display values of $W_{OW}$, $W_{CEM}$, and W/C for all combinations of observations. The equations which have been developed within this invention for use in this manner are based on the previously stated relationship whereby, $$M = 1 - (\text{VOLUME}/\text{WEIGHT})$$

Therefore, $$M_{LIQ} = 1 - \left[ \frac{W_{OW} + V_{ML} + W_{CEM}(1 - M_{CEM})}{W_{OW} + \frac{V_{ML}}{(1 - M_{ML})} + W_{CEM}} \right] \quad (1)$$

$$M_{FILT} = 1 - \left[ \frac{W_{OW} - A_{CEM}W_{CEM} + V_{ML}}{S_{CEM}(W_{OW} - A_{CEM}W_{CEM}) + \frac{V_{ML}}{(1 - M_{ML})}} \right] \quad (2)$$

where symbols denote the following:
$M_{LIQ}$ = Buoyancy point of the Liquor
$M_{FILT}$ = Buoyancy point of the Filtrate
$M_{CEM}$ = Buoyancy point of the Cement
$M_{ML}$ = Buoyancy point of the special mixing liquid added to the concrete sample
$W_{OW}$ = Weight (or Volume) of the original water in the concrete sample
$W_{CEM}$ = Weight of the cement in the concrete sample
$V_{ML}$ = Volume of the special mixing liquid added to the concrete sample
$A_{CEM}$ = Absorption factor of the cement
$S_{CEM}$ = Solubility factor of the cement The solving of the equations is possible because all values except $W_{OW}$ and $W_{CEM}$ are known after the process which yields $M_{LIQ}$ and $M_{FILT}$. Simultaneous solution of the two equations, with two unknowns, is a simple matter. Rapid results can be obtained under many variable conditions using graphical representations or hand-held programmable calculators.

The water/cement ratio is obtained simply by dividing $W_{OW}$ by $W_{CEM}$. Many other properties of the concrete mix can be determined if the concrete sample is weighed prior to mixing with the special liquid and the aggregate residue is again weighed after washing away all other constituents. The weighing of the residue aggregate in the original volumetric flask full of water will yield information concerning the amount of aggregate and air in the original concrete sample.

It should be noted that equation (2) above, is based on the assumption that no cement constituents are dissolved by the special mixing liquid. This is true in the case that the special mixing liquid is not a solvent for the cement or in case the special mixing liquid has been presaturated with the soluble constituents of the cement. The latter is true in the preferred special mixing liquid described herein. It is also possible to write equation (2) to include the effect of cement solution by the special mixing liquid.

When the weight of cement, weight of original water and water/cement ratio of the concrete sample have been made known, the principle objectives of this invention have been achieved. The results of the process can, however, be extrapolated to provide additional information about the proportion of other ingredients in the concrete mixture. These include the amount of air and aggregate in a unit volume of concrete.

The process of this invention is performed with completely liquid samples. No drying or sieving is required. The equipment necessary, as described, is relatively light, inexpensive and transportable. The adjustable range hydrometer measurements are accurate and easily obtainable over a wide range of values and the computation of results is reasonably simple. This process is well suited to field measurements.

Although the process and equipment for this invention have been described with reference to a particular embodiment thereof, it should be understood that those skilled in the art may make other modifications and embodiments thereof which will fall within the spirit and scope of the principles of this invention.

What is claimed as new and desired to be secured by patent of the United States is:
1. A process for analyzing the water and cement content of a concrete mixture comprising the steps of:
   (a) mixing a known volume of the concrete mixture with a known volume of a mixing liquid miscible in water and having a known density other than water;
   (b) filtering the mixture of cement, water and mixing liquid to remove the aggregate and measuring the density of the resulting liquor;
   (c) filtering the liquor to remove the cement and measuring the density of the resulting filtrate
   (d) using the measured densities to calculate the weight of cement and water in the original concrete sample and therefore the water to cement ratio.

* * * * *